(12) United States Patent
Kagan et al.

(10) Patent No.: US 9,327,064 B2
(45) Date of Patent: May 3, 2016

(54) MEMBRANES, SYSTEMS, AND METHODS FOR APPLYING REDUCED PRESSURE TO A SUBCUTANEOUS TISSUE SITE

(75) Inventors: Jonathan Kagan, Hopkins, MN (US); Douglas A Cornet, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 720 days.

(21) Appl. No.: 12/643,856

(22) Filed: Dec. 21, 2009

(65) Prior Publication Data

US 2010/0160877 A1    Jun. 24, 2010

Related U.S. Application Data

(60) Provisional application No. 61/140,657, filed on Dec. 24, 2008.

(51) Int. Cl.
*A61M 1/00* (2006.01)
*A61F 13/02* (2006.01)
*A61F 13/00* (2006.01)

(52) U.S. Cl.
CPC ........ *A61M 1/0088* (2013.01); *A61F 13/00068* (2013.01); *A61F 13/0203* (2013.01);
(Continued)

(58) Field of Classification Search
CPC . A61M 27/00; A61M 1/008; A61M 2027/00; A61M 27/002; A61F 13/00068; A61F 13/15; A61F 13/36; A61F 13/45; A61F 2013/00089; A61F 2013/00157; A61F 2013/00217; A61F 2013/0028; A61F 2013/00357; A61F 2013/00221; A61F 2210/0004; A61F 2013/00536; A61F 2013/00327; A61F 13/0203; A61F 13/0206; A61F 13/0213; A61F 13/0216; A61F 13/022; A61F 13/0223; A61F 13/0226; A61F 2013/0054; A61F 2013/00251; A61F 2013/49023; A61F 2013/51078; A61F 2013/5108; A61F 2013/51083; A61F 2013/51085; A61F 2013/51088; A61F 13/51476; A61F 2013/00859; A61F 2013/00863; A61L 15/64; A61L 15/425; A61L 15/60; A61L 15/62
USPC .......... 604/319, 540, 541, 543, 320, 304, 305
See application file for complete search history.

(56) References Cited

U.S. PATENT DOCUMENTS 1,355,846 A    10/1920    Rannells
2,177,490 A  * 10/1939    Kieffer .......................... 428/185
(Continued)

FOREIGN PATENT DOCUMENTS

AU    550575 A1    8/1982
AU    745271       4/1999
(Continued)

OTHER PUBLICATIONS

Dodson, C. T. J., Y. Oba, and W. W. Sampson. "Bivariate normal thickness-density structure in real near-planar stochastic fiber networks." Journal of Statistical Physics 102.1-2 (2001): 345-353.*
(Continued)

*Primary Examiner* — Adam Marcetich

(57) ABSTRACT

The illustrative embodiments described herein are directed to apparatuses, systems, and methods for applying reduced pressure to a subcutaneous tissue site. In one illustrative embodiment, the apparatus includes a membrane having a substantially uniform membrane wall thickness and a first, tissue-facing surface. The membrane may be shaped to form a plurality of protrusions on the tissue-facing surface. The plurality of protrusions at least partially defines at least one channel operable to transfer the reduced pressure along the tissue-facing surface.

31 Claims, 6 Drawing Sheets

(52) U.S. Cl.
CPC ...... *A61M1/0023* (2013.01); *A61F 2013/0028* (2013.01); *A61F 2013/00089* (2013.01); *A61F 2013/00221* (2013.01); *A61F 2013/00327* (2013.01)

(56) References Cited

U.S. PATENT DOCUMENTS

| | | | |
|---|---|---|---|
| 2,547,758 A | 4/1951 | Keeling | |
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 3,832,267 A * | 8/1974 | Liu | 428/167 |
| 3,992,162 A * | 11/1976 | Gewiss | 428/604 |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,343,848 A * | 8/1982 | Leonard, Jr. | 428/156 |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,533,352 A * | 8/1985 | Van Beek | A61B 19/00 604/313 |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielson | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,711,781 A * | 12/1987 | Nick et al. | 424/446 |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt et al. | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,554,145 A * | 9/1996 | Roe et al. | 604/385.3 |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 5,695,595 A * | 12/1997 | Van Hout et al. | 264/310 |
| 5,807,295 A * | 9/1998 | Hutcheon et al. | 602/42 |
| 5,993,432 A * | 11/1999 | Lodge et al. | 604/385.3 |
| 6,071,267 A | 6/2000 | Zamierowski | |
| 6,090,089 A * | 7/2000 | Tsuji et al. | 604/385.01 |
| 6,135,116 A | 10/2000 | Vogel et al. | |
| 6,241,747 B1 | 6/2001 | Ruff | |
| 6,287,316 B1 | 9/2001 | Agarwal et al. | |
| 6,296,863 B1 * | 10/2001 | Trogolo et al. | 424/404 |
| 6,345,623 B1 | 2/2002 | Heaton et al. | |
| 6,420,622 B1 * | 7/2002 | Johnston et al. | 602/41 |
| 6,482,491 B1 * | 11/2002 | Samuelsen et al. | 428/40.1 |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,585,767 B1 * | 7/2003 | Holley et al. | 623/2.41 |
| 6,626,891 B2 | 9/2003 | Ohmstede | |
| 6,752,794 B2 * | 6/2004 | Lockwood et al. | 604/313 |
| 6,814,079 B2 | 11/2004 | Heaton et al. | |
| 7,754,937 B2 * | 7/2010 | Boehringer et al. | 602/53 |
| 7,896,856 B2 * | 3/2011 | Petrosenko et al. | 604/313 |
| 8,057,447 B2 * | 11/2011 | Olson et al. | 604/313 |
| 2002/0077661 A1 | 6/2002 | Saadat | |
| 2002/0082567 A1 * | 6/2002 | Lockwood et al. | 604/307 |
| 2002/0115951 A1 | 8/2002 | Norstrem et al. | |
| 2002/0120185 A1 | 8/2002 | Johnson | |
| 2002/0128578 A1 * | 9/2002 | Johnston et al. | 602/43 |
| 2002/0143286 A1 | 10/2002 | Tumey | |
| 2003/0059574 A1 | 3/2003 | Thomas | 428/156 |
| 2005/0209574 A1 * | 9/2005 | Boehringer et al. | 604/289 |
| 2005/0283105 A1 | 12/2005 | Heaton et al. | |
| 2006/0094997 A1 * | 5/2006 | Kurata | 602/41 |
| 2007/0016152 A1 * | 1/2007 | Karpowicz et al. | 604/326 |
| 2007/0172157 A1 * | 7/2007 | Buchman | 383/63 |
| 2007/0185426 A1 * | 8/2007 | Ambrosio et al. | 602/43 |
| 2007/0219489 A1 | 9/2007 | Johnson et al. | |
| 2007/0219585 A1 * | 9/2007 | Cornet et al. | 606/221 |
| 2008/0033324 A1 | 2/2008 | Cornet et al. | |
| 2008/0177253 A1 * | 7/2008 | Boehringer et al. | 604/543 |
| 2008/0275409 A1 | 11/2008 | Kane et al. | |
| 2009/0012483 A1 * | 1/2009 | Blott | A61M 1/0088 604/315 |
| 2009/0093779 A1 * | 4/2009 | Riesinger | 604/290 |
| 2009/0299255 A1 * | 12/2009 | Kazala et al. | 602/53 |
| 2010/0160874 A1 * | 6/2010 | Robinson et al. | 604/313 |
| 2010/0249733 A9 * | 9/2010 | Blott | A61B 17/7092 604/315 |
| 2010/0262096 A1 * | 10/2010 | Hall | A61F 13/0203 604/319 |

(56) References Cited

U.S. PATENT DOCUMENTS

| | | | | |
|---|---|---|---|---|
| 2010/0280469 | A1* | 11/2010 | Hall | A61M 1/0088 604/319 |
| 2010/0286635 | A1* | 11/2010 | Watson, Jr. | A61F 13/0203 604/305 |
| 2011/0106030 | A1* | 5/2011 | Scholz | 604/319 |

FOREIGN PATENT DOCUMENTS

| | | | | |
|---|---|---|---|---|
| AU | 755496 | | 2/2002 | |
| CA | 2005436 | | 6/1990 | |
| DE | 26 40 413 | A1 | 3/1978 | |
| DE | 43 06 478 | A1 | 9/1994 | |
| DE | 295 04 378 | U1 | 10/1995 | |
| EP | 0100148 | A1 | 2/1984 | |
| EP | 0117632 | A2 | 9/1984 | |
| EP | 0161865 | A2 | 11/1985 | |
| EP | 0358302 | A2 | 3/1990 | |
| EP | 1018967 | B1 | 8/2004 | |
| GB | 692578 | | 6/1953 | |
| GB | 2 195 255 | A | 4/1988 | |
| GB | 2 197 789 | A | 6/1988 | |
| GB | 2 220 357 | A | 1/1990 | |
| GB | 2 235 877 | A | 3/1991 | |
| GB | 2 333 965 | A | 8/1999 | |
| GB | 2 329 127 | B | 8/2000 | |
| JP | 4129536 | | 4/1992 | |
| SG | 71559 | | 4/2002 | |
| WO | WO 80/02182 | | 10/1980 | |
| WO | WO 87/04626 | | 8/1987 | |
| WO | WO 90/10424 | | 9/1990 | |
| WO | WO 93/09727 | | 5/1993 | |
| WO | WO 94/20041 | | 9/1994 | |
| WO | WO 96/05873 | | 2/1996 | |
| WO | WO 97/18007 | | 5/1997 | |
| WO | WO 99/13793 | | 3/1999 | |
| WO | WO 00/30567 | A2* | 6/2000 | A61F 2/24 |
| WO | WO 00/32247 | A2* | 6/2000 | A01N 25/34 |
| WO | WO2006114648 | | 2/2006 | |
| WO | WO2007106590 | A2 | 9/2007 | |
| WO | WO2007106594 | | 9/2007 | |
| WO | WO 2008/104609 | A1* | 9/2008 | A61M 1/00 |

OTHER PUBLICATIONS

International Search Report and Written Opinion date mailed Jul. 30, 2010 for PCT Application No. PCT/US2009/069063.
N.A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University, Cheboksary, U.S.S.R. 1986);pp. 94-96 (and certified translation).
Louis C. Argenta, MD and Michael J. Morykwas, PhD; "Vacuum-Assisted Closure: A New Method for Wound Control and Treatment: Clinical Experience"; Annals of Plastic Surgery, vol. 38, No. 6, Jun. 1997; pp. 563-576.
Susan Mendez-Eastmen, RN; "When Wounds Won't Heal" RN Jan. 1998, vol. 61 (1); Medical Economics Company, Inc., Montvale, NJ, USA; pp. 20-24.
James H. Blackburn, II, MD, et al; "Negative-Pressure Dressings as a Bolster for Skin Grafts"; Annals of Plastic Surgery, vol. 40, No. 5, May 1998, pp. 453-457.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinović, V. Đukio, Ž. Maksimović, Đ. Radak, and P. Peš ka, "Vacuum Therapy in the Treatment of Peripheral Blood Vessels," Timok Medical Journal 11 (1986), pp. 161-164 (and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.

(56) References Cited

OTHER PUBLICATIONS

M.J. Morykwas, L.C. Argenta, E.I. Shelton-Brown, and W. McGuirt, "Vacuum-Assisted Closure: A New Method for Wound Control and Treatment: Animal Studies and Basic Foundation," *Annals of Plastic Surgery* 38 (1997), pp. 553-562 (Morykwas I).

C.E. Tennants, "The Use of Hypermia in the Postoperative Treatment of Lesions of the Extremities and Thorax," *Journal of the American Medical Association* 64 (1915), pp. 1548-1549.

Selections from W. Meyer and V. Schmieden, *Bier's Hyperemic Treatment in Surgery, Medicine, and the Specialties: A Manual of Its Practical Application*, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II"), Jun. 18, 2012.

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians (Jul. 2007).

International Preliminary Report on Patentability issued Jun. 29, 2011 for PCT Application No. PCT/US2009/069063.

\* cited by examiner

MEMBRANES, SYSTEMS, AND METHODS FOR APPLYING REDUCED PRESSURE TO A SUBCUTANEOUS TISSUE SITE

CROSS-REFERENCE TO RELATED APPLICATIONS

This application claims the benefit of U.S. Provisional Application No. 61/140,657, filed Dec. 24, 2008, which is hereby incorporated by reference.

BACKGROUND

1. Field of the Invention

The present application relates generally to medical treatment systems, and more particular, to a membrane, system, and method for applying reduced pressure to a subcutaneous tissue site.

2. Description of Related Art

Clinical studies and practice have shown that providing a reduced pressure in proximity to a tissue site augments and accelerates the growth of new tissue at the tissue site. The applications of this phenomenon are numerous, but one particular application of reduced pressure involves treating wounds. This treatment (frequently referred to in the medical community as "negative pressure wound therapy," "reduced pressure therapy," or "vacuum therapy") provides a number of benefits, including migration of epithelial and subcutaneous tissues, improved blood flow, and micro-deformation of tissue at the wound site. Together these benefits result in increased development of granulation tissue and faster healing times. Typically, reduced pressure is applied by a reduced pressure source to tissue through a porous pad or other manifold device. In many instances, wound exudate and other liquids from the tissue site are collected within a canister to prevent the liquids from reaching the reduced pressure source.

SUMMARY

The problems presented by existing reduced pressure systems are solved by the systems and methods of the illustrative embodiments described herein. In one embodiment, a system for applying reduced pressure to a tissue site is provided. The system includes a reduced-pressure source operable to supply reduced pressure and a membrane having a plurality of projections on a first, tissue-facing surface and a plurality of substantially matched recesses on a second surface of the membrane. The plurality of projections at least partially defines at least one channel operable to transfer the reduced pressure along the tissue-facing surface. The system further includes a delivery tube coupled to the membrane. The delivery tube is operable to deliver the reduced pressure to the tissue-facing surface of the membrane.

In another embodiment, a system for applying reduced pressure to a tissue site is provided. The system includes a reduced-pressure source operable to supply reduced pressure and a membrane having a plurality of non-planar, matched deviations on opposite sides of the membrane. The membrane includes at least one channel operable to transfer the reduced pressure along a first, tissue-facing side of the membrane. A delivery tube is coupled to the membrane and is operable to deliver the reduced pressure to the tissue-facing surface of the membrane.

In another embodiment, a system for applying reduced pressure to a subcutaneous tissue site includes a reduced-pressure source operable to supply reduced pressure and a membrane having a substantially uniform membrane wall thickness. The membrane includes a first, tissue-facing surface and is shaped to form a plurality of protrusions on the tissue-facing surface. The plurality of protrusions at least partially defines at least one channel operable to transfer the reduced pressure along the tissue-facing surface. A delivery tube is coupled to the membrane and is operable to deliver the reduced pressure to the tissue-facing surface of the membrane.

In another embodiment, an apparatus for applying reduced pressure to a subcutaneous tissue site includes a membrane having a substantially uniform membrane wall thickness and a first, tissue-facing surface. The membrane is shaped to form a plurality of protrusions on the tissue-facing surface, and the plurality of protrusions at least partially defines at least one channel operable to transfer reduced pressure along the tissue-facing surface.

In still another embodiment, a method for applying reduced pressure to a subcutaneous tissue site includes applying a membrane to the subcutaneous tissue site. The membrane has a substantially uniform membrane wall thickness and a first, tissue-facing surface. The membrane is shaped to form a plurality of protrusions on the tissue-facing surface, the plurality of protrusions at least partially defining at least one channel operable to transfer reduced pressure along the tissue-facing surface. The method further includes supplying the reduced pressure to the tissue-facing surface of the membrane via a delivery tube that is coupled to the membrane.

In still another embodiment, a method of manufacturing an apparatus for applying reduced pressure to a subcutaneous tissue site includes forming a membrane having a substantially uniform membrane wall thickness and a first, tissue-facing surface. The membrane is shaped to form a plurality of protrusions on the tissue-facing surface. The plurality of protrusions at least partially define at least one channel operable to transfer the reduced pressure along the tissue-facing surface.

Other objects, features, and advantages of the illustrative embodiments will become apparent with reference to the drawings and detailed description that follow.

DETAILED DESCRIPTION OF THE PREFERRED EMBODIMENTS

In the following detailed description of several illustrative embodiments, reference is made to the accompanying drawings that form a part hereof, and in which is shown by way of illustration specific preferred embodiments in which the invention may be practiced. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

The term "reduced pressure" as used herein generally refers to a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure associated with tissue at the tissue site. Although the terms "vacuum" and "negative pressure" may be used to describe the pressure applied to the tissue site, the actual pressure reduction applied to the tissue site may be significantly less than the pressure reduction normally associated with a complete vacuum. Reduced pressure may initially generate fluid flow in the area of the tissue site. As the hydrostatic pressure around the tissue site approaches the desired reduced pressure, the flow may subside, and the reduced pressure is then maintained. Unless otherwise indicated, values of pressure stated herein are gauge pressures. Similarly, references to increases in reduced pressure typically refer to a decrease in absolute pressure, while decreases in reduced pressure typically refer to an increase in absolute pressure.

Figure 1A:
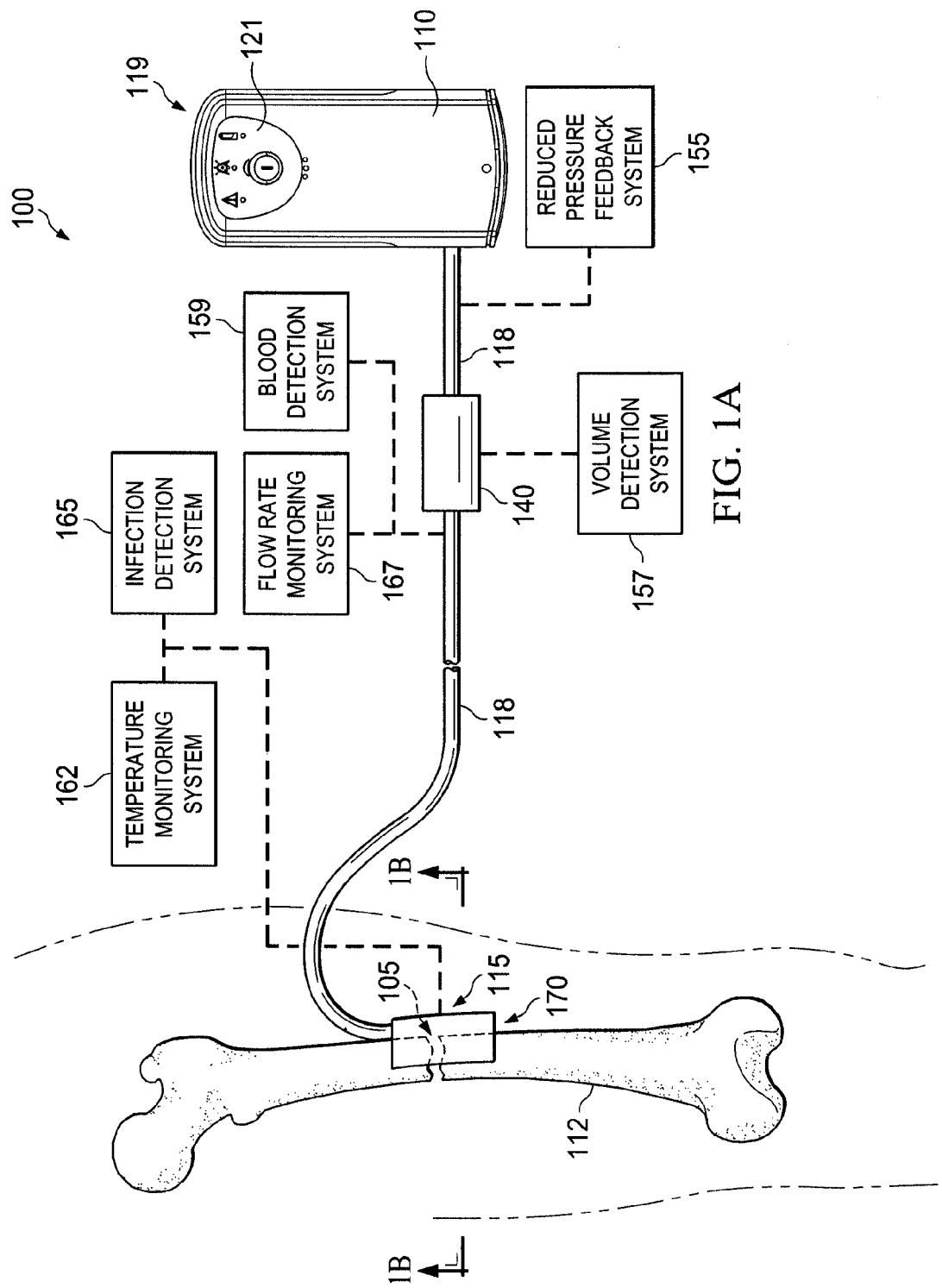
FIG. 1A illustrates a schematic of a reduced-pressure treatment system for applying reduced pressure to a tissue site according to an illustrative embodiment.
Figure 1B:
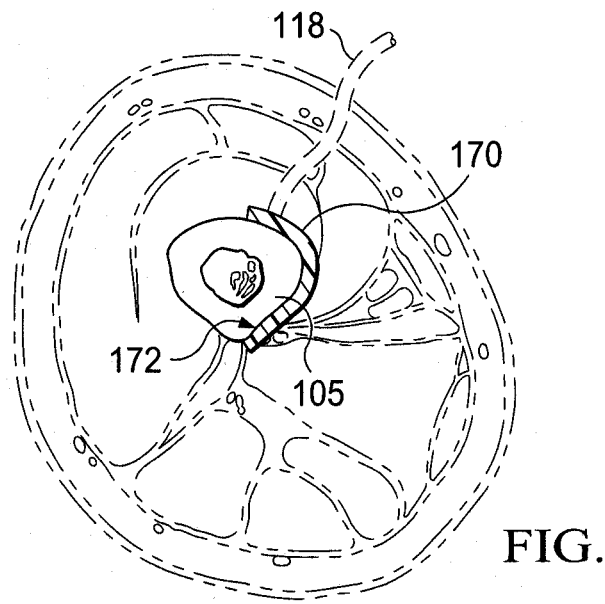
FIG. 1B illustrates a cross-sectional view of a portion of the reduced-pressure treatment system of FIG. 1A taken along line 1B-1B.

Referring to FIGS. 1A and 1B, a reduced-pressure treatment system 100, which applies reduced pressure to a tissue site 105, is shown according to an illustrative embodiment. In the embodiment illustrated in FIG. 1A, the tissue site 105 is a bone tissue site; in particular, the tissue site 105 is a fracture on bone 112, which, for example, is shown as a femur. When used to promote bone tissue growth, reduced-pressure treatment can increase the rate of healing associated with a fracture, a non-union, a void, or other bone defects. Reduced-pressure treatment may also be used to improve recovery from osteomyelitis. The treatment may further be used to increase localized bone densities in patients suffering from osteoporosis. Finally, reduced-pressure treatment may be used to speed and improve osseointegration of orthopedic implants, such as hip implants, knee implants, and fixation devices.

While tissue site 105 is bone tissue, the term "tissue site" as used herein may refer to a wound or defect located on or within any tissue, including but not limited to, bone tissue, adipose tissue, muscle tissue, neural tissue, dermal tissue, vascular tissue, connective tissue, cartilage, tendons, or ligaments. The term "tissue site" may further refer to areas of any tissue that are not necessarily wounded or defective, but are instead areas in which it is desired to add or promote the growth of additional tissue. For example, reduced pressure tissue treatment may be used in certain tissue areas to grow additional tissue that may be harvested and transplanted to another tissue location.

Referring to FIG. 1, a reduced pressure treatment system 100 includes a reduced pressure source 110 and a reduced pressure dressing 115 that is positioned at the tissue site 105. In one embodiment, the reduced pressure dressing 115 may include a membrane or manifold 170 positioned at a subcutaneous tissue site, such as tissue site 105. In another embodiment in which reduced pressure may be applied to a surface wound or a wound accessed through surgical or direct visualization techniques, the reduced pressure dressing 115 may also include a cover that may be positioned over the membrane 170. The cover, which is described in more detail below, may be used to seal the membrane 170 at the tissue site and maintain reduced pressure at the tissue site 105. The reduced pressure dressing 115 is fluidly connected to the reduced pressure source 110 by a conduit 118, and a canister 140 may be fluidly connected to the conduit 118 to receive wound exudate or other fluids drawn from the tissue site 105 by the reduced pressure source 110. The conduit 118 may be any tube through which a gas, liquid, gel, or other fluid may flow as is described in more detail below.

The membrane 170 is adapted to contact or cover the tissue site 105. As used herein, the term "cover" includes partially or fully covering. Also, a first object that covers a second object may directly or indirectly touch the second object, or may not touch the second object at all.

In one embodiment, the membrane 170 may be made from a flexible material such that the membrane 170 may be bent to fit against the tissue site 105. In the example of FIGS. 1A and 1B, the membrane 170 is curved against the contour of the tissue site 105 so that a tissue-facing surface 172 of the membrane 170 is in contact with the tissue site 105. In another embodiment, the membrane 170 may be made from a rigid material that is resistant to bending. In the case of a flexible membrane, the membrane 170 may have sufficient rigidity to resist collapse when exposed to reduced pressure, yet still maintain relative flexibility for certain applications, such as for percutaneous insertion and placement at the subcutaneous tissue site 105. Additional embodiments described below show that the membrane 170 may include protrusions and channels on the tissue-facing surface 172 of the membrane 170.

As previously mentioned, the reduced pressure generated by the reduced-pressure source 110 may be provided to the membrane 170 by conduit 118. In particular, conduit 118 may deliver reduced pressure from the reduced-pressure source 110 to the tissue-facing surface 172 of the membrane 170 during treatment. Conduit 118 may be coupled to the membrane 170. As used throughout, the term "coupled" includes coupling via a separate object. For example, conduit 118 is coupled to the membrane 170 if both conduit 118 and the membrane 170 are coupled to one or more third objects. The term "coupled" also includes "directly coupled," in which case the two objects touch each other in some way. The term "coupled" also encompasses two or more components that are continuous with one another by virtue of each of the components being formed from the same piece of material. The term "coupled" includes chemical coupling, such as via a chemical bond. The term "coupled" also includes fluidly coupled, in which case a first object that is coupled to a second object is in fluid communication with that second object. The term "coupled" may also include mechanical, thermal, or electrical coupling. Objects that are "coupled" may also be fixedly or removably coupled.

The conduit 118 may be made from any material, and may be either flexible or inflexible. The conduit 118 may include one or more paths or lumens through which fluid may flow. For example, the conduit 118 may include two or more lumens, one of which may be used to deliver reduced pressure to the tissue site and one of which may be used to determine the level of reduced pressure at the tissue site 105. Alternatively, one of the lumens may be used to deliver fluids, such as air, antibacterial agents, antiviral agents, cell-growth promotion agents, irrigation fluids, or other chemically active agents, to the tissue site 105.

In the embodiment illustrated in FIG. 1A, the reduced pressure source 110 is an electrically-driven vacuum pump. In another implementation, the reduced pressure source 110 may instead be a manually-actuated or manually-charged pump that does not require electrical power. The reduced pressure source 110 instead may be any other type of reduced pressure pump, or alternatively a wall suction port such as those available in hospitals and other medical facilities. The reduced pressure source 110 may be housed within or used in conjunction with a reduced pressure treatment unit 119, which may also contain sensors, processing units, alarm indicators, memory, databases, soft ware, display units, and user interfaces 121 that further facilitate the application of reduced pressure treatment to the tissue site 105. In one example, a sensor or switch (not shown) may be disposed at or near the reduced pressure source 110 to determine a source pressure generated by the reduced pressure source 110. The sensor may communicate with a processing unit that monitors and controls the reduced pressure that is delivered by the reduced pressure source 110.

The reduced-pressure treatment system 100 may include a reduced pressure feedback system 155 operably associated with the other components of the reduced-pressure treatment system 100 to provide information to a user of the reduced-pressure treatment system 100 indicating a relative or absolute amount of pressure that is being delivered to the tissue site 105 or that is being generated by the reduced-pressure source 110. Examples of feedback systems include, without limitation, pop valves that activate when the reduced pressure rises above a selected value and deflection pop valves.

The reduced-pressure treatment system 100 may include a volume detection system 157 to detect the amount of fluid present in the canister 140, a blood detection system 159 to detect the presence of blood in exudate drawn from the tissue site 105 (including the exudate that is present in the canister 140), a temperature monitoring system 162 to monitor the temperature of the tissue site 105, an infection detection system 165 to detect the presence of infection at the tissue site 105, and/or a flow rate monitoring system 167 to monitor the flow rate of fluids drawn from tissue site 105. The infection detection system 165 may include a foam or other substance that changes color in the presence of bacteria. The foam or other substance may be operably associated with the dressing 115 or the conduit 118 such that the color changing material is exposed to exudate from the tissue site 105. In addition to the above-mentioned components and systems, the reduced-pressure treatment system 100 may include valves, regulators, switches, and other electrical, mechanical, and fluid components to facilitate administration of reduced-pressure treatment to the tissue site 105.

Figure 2:
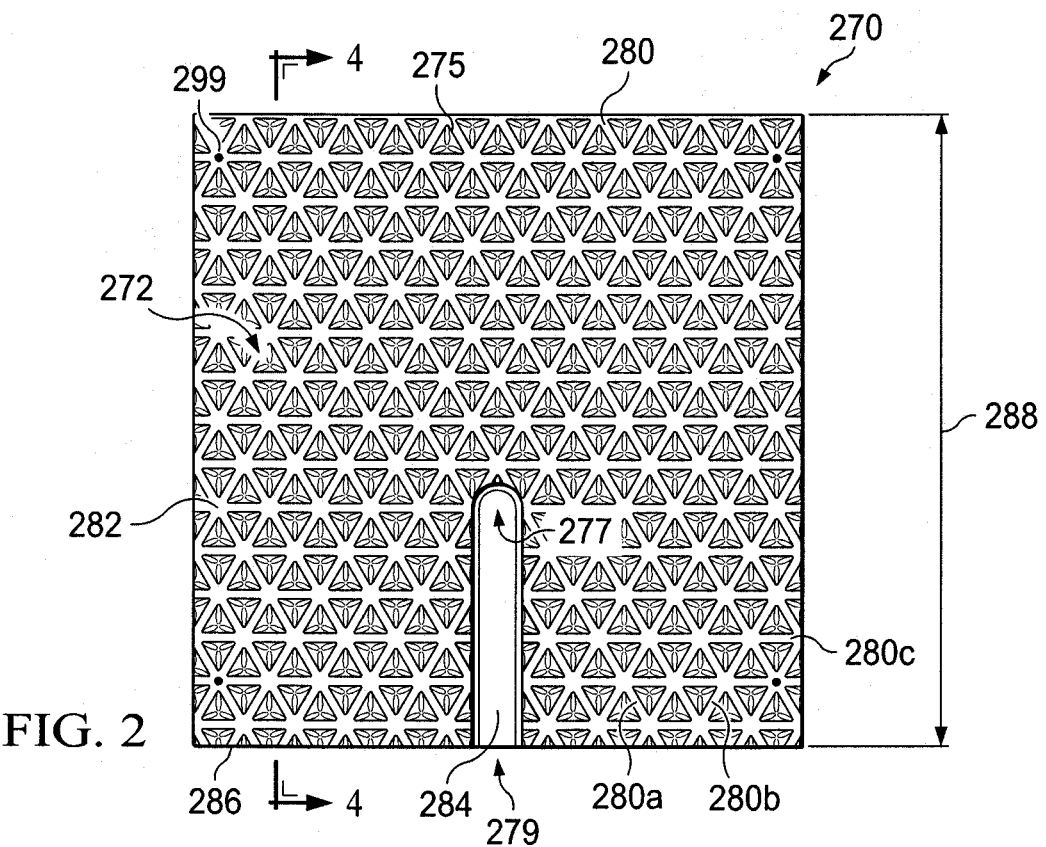
FIG. 2 illustrates a top view of a membrane or manifold for applying reduced pressure to a tissue site according to an illustrative embodiment.
Figure 3:
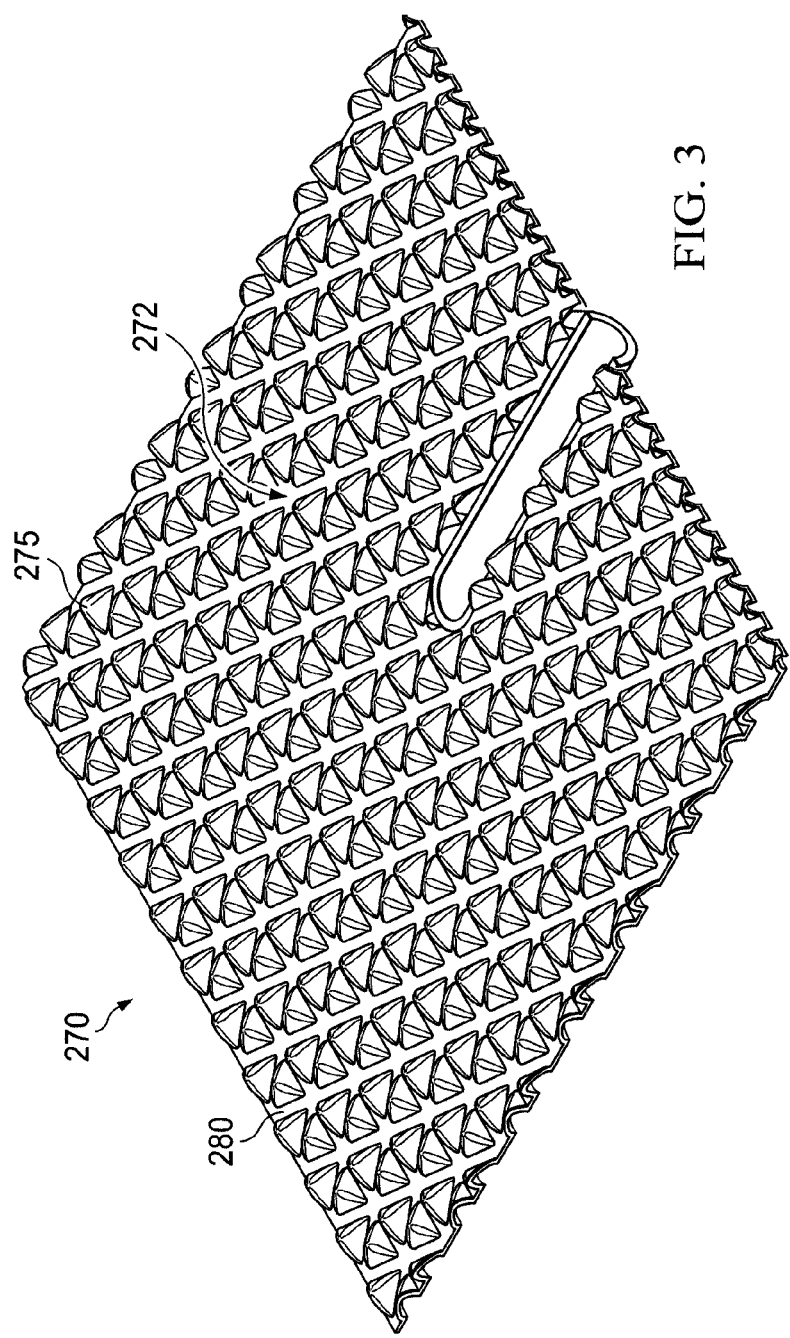
FIG. 3 illustrates a perspective view of the membrane of FIG. 2.
Figure 4:
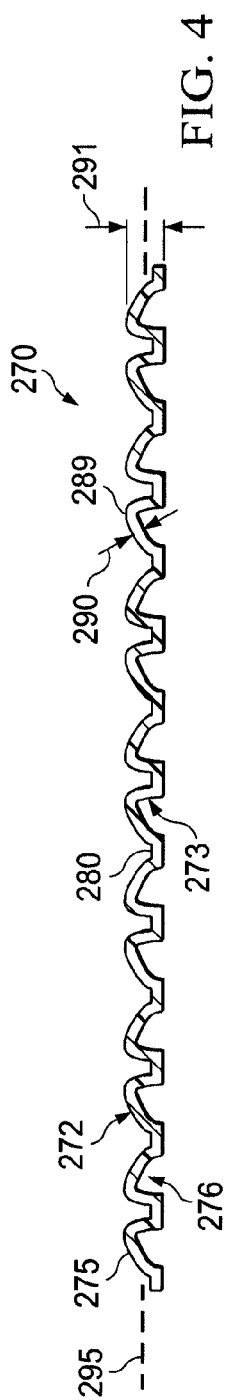
FIG. 4 illustrates a cross-sectional side view of the membrane of FIG. 2 taken along line 4-4.

Referring to FIGS. 2-4, a membrane 270 according to an illustrative embodiment includes a first, tissue-facing side or surface 272 having a plurality of protrusions 275 on the first, tissue-facing surface 272. The protrusions 275 have a substantially triangular shape as viewed in FIG. 2; however, in other embodiments, the protrusions 275 may have any shape. The protrusions 275 are operable to contact a subcutaneous tissue site, such as tissue site 105 in FIG. 1A.

The membrane 270 also includes a second side or surface 273 opposite the first, tissue-facing surface 272. In one embodiment, each of the protrusions 275 forms a respective recess 276 on the second surface 273.

The protrusions 275 at least partially define at least one channel. In the illustrative embodiment of FIGS. 2-4, the protrusions 275 define channels 280. The channels 280 are interconnected, and are formed between the protrusions 275. The channels 280 include slanted channels 280a and 280b, which have an angled or diagonal orientation, as well as lateral channels 280c, which, in the illustrated embodiment, are substantially perpendicular to at least one edge of the membrane 270. The channels 280 intersect at intersection portions 282. The protrusions 275 may form discontinuous wall members that define channels according to various patterns. In the embodiment of FIGS. 2-4, channels radially emanate from the intersection portions 282 in six directions. However, channels may emanate, radially or otherwise, from intersection portions 282 in any number of directions.

The channels 280 are operable to transfer reduced pressure, and the flow of any fluids due to the application of reduced pressure, along the first, tissue-facing surface 272. The reduced pressure may be provided by a reduced-pressure source, such as reduced-pressure source 110 in FIG. 1A. The reduced pressure may be delivered to the membrane 270 via a delivery tube, such as conduit 118 in FIG. 1A. The channels 280 may also transfer liquid, such as exudate, along the first, tissue-facing surface 272 of the membrane 270. The liquid may be drawn into the delivery tube using the reduced pressure, and may be stored in a fluid collection apparatus, such as canister 140 in FIG. 1A.

The delivery tube or conduit may be at least partially disposed in a groove 284 disposed on the tissue-facing side 272 of the membrane 270. For example, the groove 284 may be a curved groove having a partially circular cross section such that a cylindrical delivery tube may fit into the groove 284. The groove 284 and cylindrical delivery tube, e.g., conduit 118, may cooperate to form an interference fit to hold the delivery tube in the groove 284. Alternatively, the conduit may be adhesively or otherwise secured to the membrane 270. The groove 284 may alternatively have a partially polygonal or partially elliptical cross section such that a delivery tube having a polygonal or elliptical cross section, respectively, may be disposed in the groove 284. The presence of the groove 284 may facilitate the placement of the membrane 270 over a tissue site by allowing a greater proportion of the first, tissue-facing surface 272 to make contact with the tissue site, including those portions of the tissue-facing surface abutting or adjacent groove 284. In one illustrative embodiment, the delivery tube may be coupled to the membrane 270 via the groove 284. The groove 284 may be shaped to receive at least a portion of a delivery tube. The groove 284 may be an open or closed passageway.

In one embodiment, the delivery tube, when disposed within the groove 284, may extend to or near a first end 277 of the groove 284. In another embodiment, the end of the delivery tube may be located anywhere between the first end 277 and a second end 279 of the groove 284.

Although the groove 284 is shown to be perpendicular to an edge 286 of the membrane 270, the groove 284 may have any orientation, such as an angled orientation, relative to the edge 286. Also, although the groove 284 is shown to be substantially centered along edge 286, the groove 284 may be located anywhere along the edge 286. The groove 284 may also be located along any of the other edges of the membrane 270. In another embodiment, the membrane 270 may have more than one groove 284. Also, the groove 284 may have any length, including a length that equals the length 288 of the membrane 270.

The membrane 270 may be made from any material, including any polymer. The membrane 270 is preferably biocompatible and may be either non-biodegradable or biodegradable (or bio-absorbable), or a combination thereof. Non-limiting examples of non-biodegradable materials from which the membrane 270 may be made include a Teflon® material and other fluoro polymers (which can be thermoplastic or thermoset), polyethylene terepthalate glycol (PETG), acrylic, polyethylene (PE), polyurethane (PU), polypropylene (PP), a thermoplastic (including all of the forgoing), silicone, a thermoset, latex, a dipped or cast material (as is latex and as PU can be) or any combination thereof. Non-limiting examples of bioabsorbable materials from which the membrane 270 may be made include PGA-polyglycolide, PLA-polyactide, PLA-PGA copolymers, including PLG-poly(lactide-co-glycolide) or DLPLG, PDS-poly(dioxanone), or any other bioabsorbable polymer, or any combination thereof.

Membrane 270 may be porous or non-porous. Non-limiting examples of porous membranes include foams and woven or non-woven fabrics (including mats and felts). Fabrics may use a variety of filaments including, for example, braided and extruded. Non-porous membranes, for example, may be cast, blown, molded, vacuum formed, dipped, or extruded.

The membrane 270 may further serve as a scaffold for new cell-growth, or a scaffold material may be used in conjunction with the membrane 270 to promote cell-growth. A scaffold is a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

In the embodiment in which the membrane 270 is composed of a bioabsorbable polymer, the membrane 270 may be applied to a subcutaneous tissue site, where the membrane 270 may remain and eventually degrade. In one embodiment, the membrane 270 may be configured for in-vivo detachability from a delivery tube, such as conduit 118 in FIG. 1A. For example, the groove 284 may be coated with a rapid-release adhesive that adheres the delivery tube to the groove 284 during application of the membrane 270 to a tissue site. The rapid-release adhesive may also adhere the delivery tube to the groove 284 during reduced pressure treatment. After a period of time, the rapid-release adhesive may release the delivery tube such that the delivery tube may be removed from the tissue site area while allowing the membrane 270 to remain and degrade at the tissue site.

When a bioabsorbable material is used to form membrane 270, it may be desirable to minimize the mass of the membrane, or at least control the distribution of mass throughout the membrane, to ensure that controlled bioabsorption takes place. In the embodiment shown in FIGS. 3 and 4, the membrane 270 may have a membrane wall 289 with a substantially uniform membrane wall thickness 290. The membrane wall thickness 290 may be contrasted to the membrane thickness 291. Providing a substantially uniform membrane wall thickness 290 is one way to help ensure that each portion of the membrane 270 degrades in approximately the same amount of time (assuming a constant bioabsorption rate).

The membrane wall thickness of a particular membrane will not always be substantially uniform. One particular method of manufacturing the membranes described herein involves vacuum forming. While vacuum forming may be particularly cost effective, the manufacturing technique will sometimes result in "low points" between protrusions being thicker than the "high points" associated with the protrusions. A similar circumstance may occur if the membrane is formed by a dipping process. Although in these circumstances the membrane wall thickness may not be substantially uniform, the benefit of having the membrane material mass well-distributed can still be obtained. As mentioned previously, and as illustrated in FIG. 4, for each protrusion 275 formed on one side of the membrane 270, a corresponding recess 276 exists on the opposite side of the membrane 270.

Stated another way, the membrane 270 may be associated with a medial plane 295 (illustrated as a line in FIG. 4) that substantially bisects the membrane thickness 291. In one embodiment, deviations from the plane 295 on one side of the membrane are substantially matched by similar deviations on another side of the membrane as illustrated in FIG. 4 to improve the distribution of mass throughout the membrane. In another embodiment, the membrane may not be associated with a medial plane, but still may include non-planar, matched deviations on opposite sides of the membrane. Matched deviations will typically be similar (but not necessarily exact) in shape and size and will be located relative to one another such that a positively extending structure on one side will correspond with a negatively extending structure on the opposite side (e.g. a projection and a recess).

The presence of matched or similar deviations on opposite sides of the membrane is different than membranes that include a substantially planar sheet from which projections extend on one side of the planar sheet. Substantially matched deviations or substantially matched projections and recesses allow customization of the force pattern applied to tissues on each side of the membrane. Reduced pressure may be communicated to both sides of the membrane 270 by either using a porous membrane material, by providing apertures in the membrane, or by providing a delivery tube or conduit on each side of the membrane.

In one embodiment, it may be desired to expose tissues on one side of the membrane to a different force pattern than tissues on the other side of the membrane. Typically, the exposure of a tissue to reduced pressure in the presence of a projection subjects the tissue to compressive forces as the tissue is pulled against the projection. Tissues exposed to reduced pressure near a recesses will typically experience tensile forces as the tissue is stretched and pulled into the recesses. It should be noted, however, that certain areas of tissue on a "projection" side of the membrane may also be subjected to tensile forces if these areas of tissue are pulled into the channels or depressions between projections. Similarly, the channels or depressions may act similar to projections on the "recess" side of the membrane, thereby subjecting tissues adjacent the areas between recesses to compressive forces.

Projection and recess geometry may be selected for increased or reduced tissue compression or increased or reduced tissue tension. Sharper projections can increase compression over a small area while broader projections can distribute the compression over a larger area. Similarly, larger recesses can increase the tension seen be tissues. These effects will be dependent on tissue mechanical properties as well as geometry. It should be noted that the projections on one side of the membrane may be shaped to be more sharply defined or pointed, and the recesses corresponding with each of these projections could be shaped to be more rounded or dull. Similarly, the projections could be shaped more broadly or rounded, and the recesses shaped more sharply to further customize the force profile applied to tissue on each side of the membrane.

While embodiments have been described in which different force patterns may be applied on each side of the membrane, it should also be noted that the membrane may be designed to ensure a substantially symmetric force distribution on each side of the membrane. For example, offset projections may be provided on each side of the membrane that are similar in shape and size and that include recesses between the projections (on each side of the membrane) that are similar in shape and size. As one example of this configuration, a membrane may be provided in which the projections and recesses are defined on each side by a substantially sinusoidal cross-sectional profile. Other examples of providing a symmetric force distribution are also possible.

It should be appreciated that matching deviations on one side of the membrane with deviations on another side of the membrane (e.g. a recess associated with each projection) does not necessarily require a substantially uniform membrane wall thickness. Rather, variations in membrane wall thickness may occur. In either situation, the matched or similar deviations still assist in more evenly distributing the mass of the membrane material. This more even distribution of mass may assist in controlling the absorption of the membrane if bioabsorbable material is used.

The bioabsorbable material from which the membrane 270 may be made may also include antibiotics or growth factors. The antibiotics or growth factors may be released at the tissue site as the membrane 270 degrades. In one embodiment, the bioabsorbable material in which the antibiotics or growth factors are embedded is selected such that the antibiotics or growth factors are released at a predetermined rate. For example, a bioabsorbable material having a relatively slower rate of degradation may be selected such that the embedded antibiotics or growth factors are released at the tissue site at a relatively slower rate.

In another embodiment, the membrane 270 may include radio opaque markers 299 made from a radio opaque material, such a gold, platinum, or an alloy such as Pt/Ir. In one example, the radio opaque markers 299 may be discrete metal radio opaque markers. The radio opaque markers 299 may be applied to the membrane 270 in any manner. For example, the radio opaque markers 299 may be bonded, printed or painted on the membrane 270. The radio opaque markers 299 may also be located anywhere on or in the membrane 270. The radio opaque markers 299 facilitate the detection of the membrane 270 using x-rays. In one example, the radio opaque markers 299 may help to determine whether a membrane made from a biodegradable material has degraded. The membrane 270 may be transparent, opaque, or have both transparent and opaque characteristics.

In another example, the membrane 270 may include a radio opaque compound, such as barium sulfate or bismuth carbonate, in the resin or material used to form the membrane. Such a radio opaque compound may also be used to form the radio opaque markers 299. The radio opaque material from which the membrane 270 or the radio opaque markers 299 may be made may optionally include compounds that the body can readily absorb, degrade, or excrete (e.g., iodine or iodine compounds). The radio opaque material may also include compounds that are visible by magnetic resonance imagining (MRI), such as chelated gadolinium.

The membrane 270 may have any membrane wall thickness 290, and the thickness 290 may be chosen to achieve a desired effect. For example, if a particular duration ($T_1$) is desired for membrane 270 before the membrane 270 is absorbed and if the bio-absorption rate of the material is high, the membrane wall thickness 290 may be increased to achieve the desired duration ($T_1$) or if the bio-absorption rate of the material is relatively low, a small membrane wall thickness 290 might be used to achieve the desired duration ($T_1$). As another example, if a certain desired flexibility is desired for the membrane 270 and if the material from which the membrane wall thickness 290 is formed is relatively stiff, a relatively thin wall thickness 290 might be used to achieve the desired flexibility or if the material from which the membrane wall thickness 290 is made is relatively flexible, a thicker member wall thickness 290 might be used to achieve the desired flexibility. Controlling the material variables and properties, e.g., absorption rate, thickness, and stiffness, may be particularly applicable to clinical situations in which the resistance to collapse when exposed to a therapeutic level of reduced pressure is required and a particular duration may be desired.

In the embodiment in which the membrane 270 is made from a bioabsorbable material, the membrane wall thickness 290 of the membrane 270 may be chosen to adjust the length of time needed for the membrane 270 to absorb. In another embodiment, the membrane wall thickness 290 of the membrane 270 may also be chosen to adjust the amount of antibiotics or growth factors that may be contained by the membrane 270. In another embodiment, the membrane wall thickness 290 of the membrane 270 may be chosen to adjust the surface area to volume ratio of the membrane 270, thereby changing the rate at which the membrane 270 absorbs. As mentioned previously, the membrane wall thickness may or may not be substantially uniform (i.e. substantially the same thickness) throughout the membrane. In one illustrative embodiment, the membrane 270 was formed from polypropylene and had a membrane wall thickness 290 in the range of 0.005" to 0.050" and more particularly in the range of 0.010" to 0.040, and even more particularly in the range of 0.015 to 0.025, and in particular a membrane wall thickness 290 of 0.020". In another embodiment, the membrane wall thickness 290 may vary throughout the membrane such that wall thickness 290 may be, for example, thicker along channels 280a, 280b and 280c and thinner at protrusions 275.

In one embodiment, a method for applying reduced pressure to a subcutaneous tissue site may include applying a membrane as described in any of the illustrative embodiments, such as membrane 270, to the subcutaneous tissue site. The membrane 270 is applied to the subcutaneous tissue site such that the first, tissue-facing surface 272 of the membrane 270 faces the subcutaneous tissue site. The first, tissue-facing surface 272 may be in direct or indirect contact with the subcutaneous tissue site. In one embodiment, applying the membrane 270 to the subcutaneous tissue site includes bending, rolling, unrolling, or otherwise changing the shape of the membrane 270 to facilitate percutaneous insertion or subcutaneous placement of the membrane 270.

The method may also include supplying reduced pressure to the first, tissue-facing surface 272 of the membrane 270 via a delivery tube, such as conduit 118 in FIG. 1A, which is coupled to the membrane 270. The reduced pressure is from a reduced-pressure source, such as reduced-pressure source 110 in FIG. 1A. In one embodiment, the method may also include transferring the reduced pressure along the first, tissue-facing surface 272 of the membrane 270 during treatment. For example, the reduced pressure may be at least partially transferred via the channels 280; in this example, the space that is formed by the channels 280 and the tissue site may form a passage through which reduced pressure may be transferred. In embodiments where a porous material is used to form the membrane 270, reduced pressure may also be partially transferred through membrane 270 itself.

In one embodiment, a method of manufacturing an apparatus for applying reduced pressure to a subcutaneous tissue site includes forming a membrane as in any of the illustrative embodiments disclosed herein, including the membrane 270. In one embodiment, forming the membrane includes vacuum molding the membrane 270. The membrane 270 may also be formed using injection molding, compression molding, or casting. Any of these methods of forming the membrane 270 may be used to create channels, such as channels 280, in a planar membrane. Any of these methods may also facilitate the economical manufacturing of the membrane 270.

The method of manufacturing the apparatus may also include providing a delivery tube, such as conduit 118 in FIG. 1A, for delivering the reduced pressure to the first, tissue-facing surface 272 of the membrane 270. The method of manufacturing may also include coupling the delivery tube to the membrane 270 such that the delivery tube is in fluid communication with the first, tissue-facing surface 272 of the membrane 270.

Figure 5:
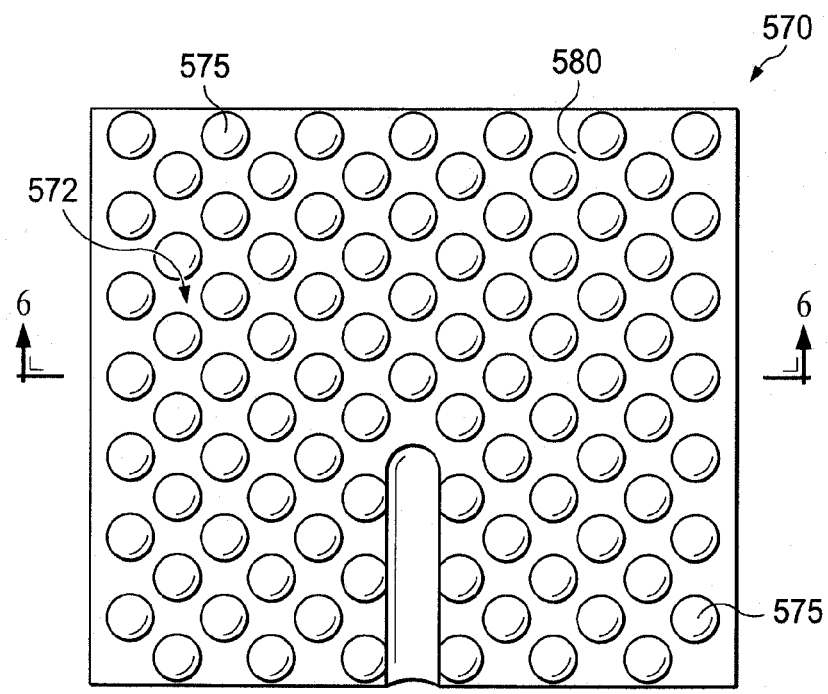
FIG. 5 illustrates a top view of a membrane or manifold for applying reduced pressure to a tissue site according to an illustrative embodiment.
Figure 6:
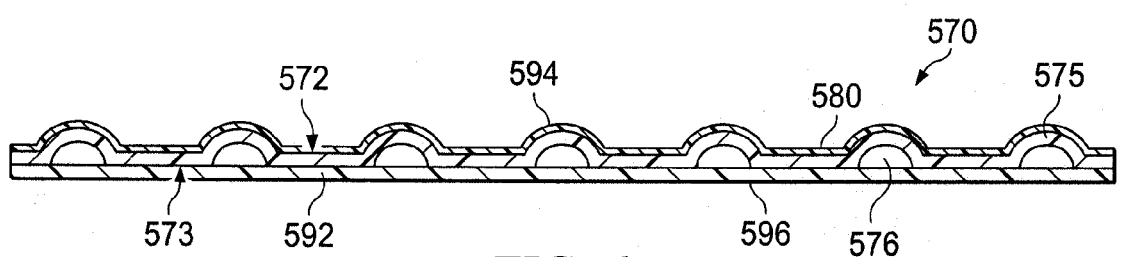
FIG. 6 illustrates a cross-sectional side view of the membrane of FIG. 5 taken along line 6-6.

Referring to FIGS. 5 and 6, a membrane 570 according to an illustrative embodiment includes a tissue-facing surface 572 having protrusions 575 that have a dome shape. Viewed from the perspective of FIG. 5, the protrusions 575 have a circular shape. In other embodiments, the protrusions 575 may have any shape as viewed in FIG. 5, including an elliptical, diamond, polygonal, or elongated shape. In the example in which the protrusions 575 have an elliptical shape as viewed in FIG. 5, the protrusions 575 may have a semi-ellipsoidal shape. In other embodiments, one or more of the protrusions 575 may have a shape that is different from the remainder of the protrusions 575.

The membrane 570 also includes channels 580, which are at least partially defined by the protrusions 575, and are analogous to channels 280 in FIGS. 2-4. The channels 580 facilitate the transfer of reduced pressure or fluids along the tissue-facing surface 572 of the membrane 570.

In one embodiment, the membrane 570, or any of the other membranes described herein, may include a backing sheet 592, which is coupled to a surface 573 of the membrane 570. The flexible backing sheet 592 may be composed of a biodegradable or non-biodegradable material, and may add strength and durability to the membrane 570. The membrane 570 may be coupled to the backing sheet 592 in any manner, such as by using welding (e.g., ultrasonic or RF), bonding, adhesives (e.g., silicone adhesive), cements, etc.

In another embodiment, the membrane 570, or any of the illustrative embodiments described herein, may include a coating 594 that at least partially covers the membrane 570. Although the coating 594 is shown in FIG. 6 to cover the tissue-facing surface 572 of the membrane 570, the coating 594 may cover any surface of the membrane 570, including the surface 573. The coating 594 may also cover any surface of the backing sheet 592, including the surface 596 of the backing sheet 592. In one embodiment, the coating 594 may be at least partially composed of a hydrogel. In this embodiment, the coating 594 of hydrogel may reduce friction at the surface of the membrane 570 that is covered by the coating 594. Thus, the coating 594 of hydrogel may facilitate the percutaneous insertion of the membrane 570 and subcutaneous application and placement of the membrane 570 at the tissue site.

In another embodiment, the coating 594 may be at least partially composed of heparin. In this embodiment, the coating 594 may reduce or prevent the formation of clots at the tissue site or elsewhere. In still another embodiment, the coating 594 may also include antibiotics or growth factors. In another embodiment, the coating 594 may also be at least partially composed of poly(ethylene glycol) (PEG).

Each of the protrusions 575 of membrane 570 form a respective hollow recess 576 along the surface 573 of the membrane 570. Each recess 576 may be filled with a material, such as the material from which the membrane 570 is made; in this example, each recess 576 is not hollow and the membrane 570 does not have a substantially uniform wall thickness. In one embodiment in which each recess 576 is filled with a material, the membrane 570 may absorb to result in a distributed array of degradable protrusions 575 (e.g., 0.60"× 0.060") after the degradation of the thinner (e.g. 0.020") portions of the membrane 570. In another embodiment, each recess 576 may include a drug, a growth factor, or an antibiotic; in this embodiment, the drug in each recess 576 may be delivered to a tissue site as the protrusions 575 of the membrane 570 absorb. In still other embodiments, the membrane 570 may have a substantially uniform membrane wall thickness or may have matched or similar deviations on opposite sides of the membrane 570 as described previously with reference to membrane 270.

Figure 7:
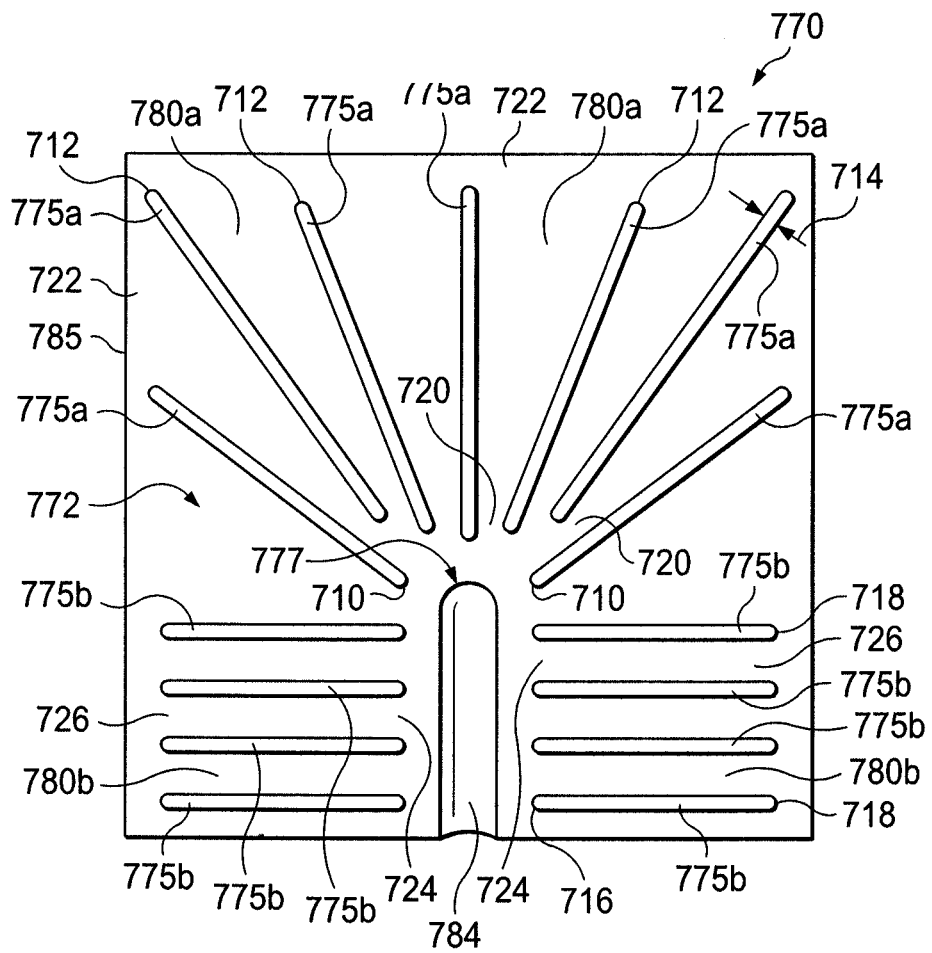
FIG. 7 illustrates a top view of a membrane or manifold for applying reduced pressure to a tissue site according to an illustrative embodiment.

Referring now to FIG. 7, a membrane 770 according to an illustrative embodiment includes a tissue-facing surface 772 showing protrusions 775a and 775b that are elongated. Each of the protrusions 775a has an end 710 and an end 712. The end 710 of each of the protrusions 775a is adjacent a groove 784. The end 712 of each of the protrusions 775a is adjacent at least one of the edges, e.g., edge 785, of the membrane 770. The protrusions 775a extend radially from near or at an end 777 of the groove 784. Any number of protrusions may extend radially from the groove 784. Also, the protrusions 775a may extend radially from portions of the groove 784 other than the end 777.

The protrusions 775a at least partially form elongated channels 780a, which may be similar to the channels 280 in FIGS. 2-4. Each of the channels 780a has a channel end 720 and a channel end 722. The channel end 720 of each of the channels 780a is adjacent the groove 784. The channel end 722 of each of the channels 780a is adjacent at least one edge of the membrane 770. The channels 780a are also tapered such that the channel end 722 is wider than the channel end 720.

The membrane 770 also includes elongated protrusions 775b, which are substantially perpendicular to the groove 784. Each of the protrusions 775b is also substantially parallel to one another. Each of the protrusions 775b has an end 716 and an end 718. The end 716 of each of the protrusions 775b is adjacent the groove 784. The end 718 of each of the protrusions 775b is adjacent at least one edge of the membrane 770.

The protrusions 775b at least partially form elongated channels 780b, which are similar to the channels 280 in FIGS. 2-4. The channels 780b are substantially perpendicular to the groove 784. Each of the channels 780b has an end 724 and an end 726. The end 724 of each of the channels 780b is adjacent the groove 784. The end 726 of each of the channels 780b is adjacent at least one edge of the membrane 770.

Each of the protrusions 775a and 775b may have any width 714. In addition, the width 714 of each of the protrusions 775a and 775b may be uniform or non-uniform. In another embodiment, at least a portion of the protrusions 775a and 775b may be tapered such that one end of the protrusions 775a and 775b, such as ends 710 and 716, respectively, may have a smaller width than the other end of the protrusions 775a and 775b, such as ends 712 and 718, respectively.

In another embodiment, all of the protrusions 775a and 775b may extend radially from a portion of the groove 784, such as the end 777 of the groove 784. In still another embodiment, the channels 780a and 780b may instead form protrusions that form channels; in this embodiment, the protrusions 775a and 775b are channels instead of protrusions.

In still other embodiments, the membrane 770 may have a substantially uniform membrane wall thickness or may have matched or similar deviations on opposite sides of the membrane 770 as described previously with reference to membrane 270.

Figure 8:
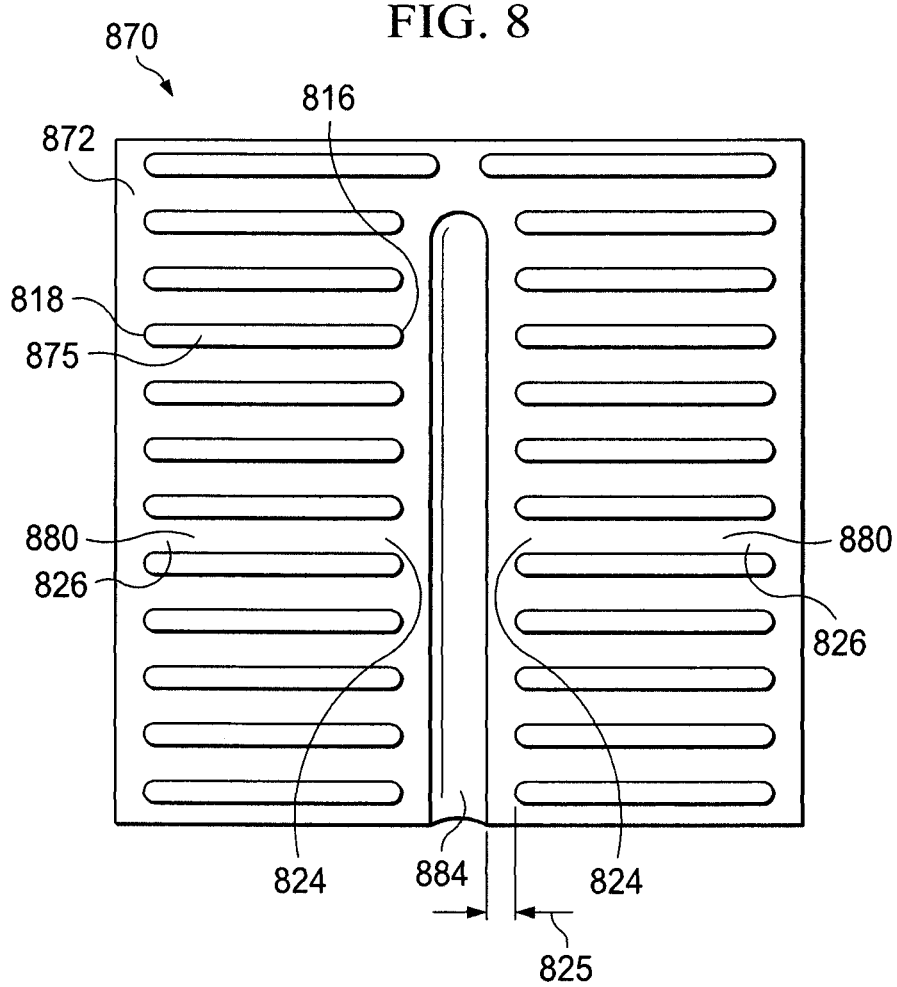
FIG. 8 illustrates a top view of a membrane or manifold for applying reduced pressure to a tissue site according to an illustrative embodiment.

Referring to FIG. 8, a membrane 870 according to an illustrative embodiment includes a tissue-facing surface 872 having protrusions 875, which are similar to the protrusions 275 in FIGS. 2-4. Each of the protrusions 875 is substantially perpendicular to a groove 884. Each of the protrusions 875 is also substantially parallel to one another. Each of the protrusions 875 has an end 816 and an end 818. The end 816 of each of the protrusions 875 is adjacent the groove 884. The end 818 of each of the protrusions 875 is adjacent at least one edge of the membrane 870.

The protrusions 875 at least partially form elongated channels 880, which are similar to the channels 280 in FIGS. 2-4. The channels 880 are substantially perpendicular to the groove 884. Each of the channels 880 is also substantially parallel to one another. Each of the channels 880 has an end 824 and an end 826. The end 824 of each of the channels 880 is adjacent the groove 884. The end 826 of each of the channels 880 is adjacent at least one edge of the membrane 870.

In one embodiment, the membrane 870 also includes gap 825 between the end 816 of each of the protrusions 875 and the groove 884. The gap 825 may be any distance, or may be omitted altogether.

In still other embodiments, the membrane 870 may have a substantially uniform membrane wall thickness or may have matched or similar deviations on opposite sides of the membrane 870 as described previously with reference to membrane 270.

It should be apparent from the foregoing that an invention having significant advantages has been provided. While the invention is shown in only a few of its forms, it is not just limited but is susceptible to various changes and modifications without departing from the spirit thereof.

We claim:

1. A system for applying reduced pressure to a subcutaneous tissue site, the system comprising:
   a reduced-pressure source operable to supply reduced pressure;
   a bioabsorbable membrane consisting essentially of
      a single membrane wall having a substantially uniform membrane wall thickness and formed with substantially no perforations;
      a plurality of projections and a plurality of substantially matched recesses formed by the membrane wall; and
   a delivery tube coupled to the membrane, the delivery tube operable to deliver the reduced pressure to a tissue-facing surface of the membrane.

2. The system of claim 1, wherein the membrane comprises a porous material.

3. The system of claim 1, wherein the plurality of projections and the plurality of substantially matched recesses allow variation of the type of force applied to tissue on opposite sides of the membrane.

4. The system of claim 3, wherein tissue adjacent the plurality of projections is subjected to compressive forces in the presence of reduced pressure.

5. The system of claim 3, wherein tissue adjacent the plurality of substantially matched recesses is subjected to tensile forces in the presence of reduced pressure.

6. The system of claim 1, wherein the plurality of projections and the plurality of substantially matched recesses deviate from a medial plane associated with the membrane.

7. The system of claim 1, wherein the plurality of projections and the plurality of substantially matched recesses have substantially triangular faces.

8. The system of claim 1, wherein the plurality of projections and the plurality of substantially matched recesses form a plurality of interconnected channels between the projections.

9. The system of claim 1, wherein:
   the membrane further comprises a groove formed on a first side of the membrane wall, the groove having a profile matching an outer dimension of the delivery tube; and
   the delivery tube is coupled to the groove.

10. The system of claim 9, wherein the groove extends from an edge of the membrane wall toward a center of the membrane wall.

11. The system of claim 9, wherein the delivery tube is coupled to the groove in an interference fit.

12. The system of claim 9, wherein an adhesive adheres the delivery tube to the groove.

13. The system of claim 12, wherein the adhesive is configured to release the delivery tube from the groove after a period of time.

14. A system for applying reduced pressure to a subcutaneous tissue site, the system comprising:
   a reduced-pressure source operable to supply reduced pressure;
   a bioabsorbable membrane consisting essentially of a single, solid, and substantially planar sheet and having a plurality of non-planar, matched deviations on opposite sides of the membrane, the membrane having at least one channel operable to transfer the reduced pressure along a first, tissue-facing side of the membrane; and
   a delivery tube coupled to the membrane, the delivery tube operable to deliver the reduced pressure to the tissue-facing surface of the membrane;
   wherein a membrane wall thickness associated with the membrane is substantially uniform throughout the membrane.

15. The system of claim 14, wherein the matched deviations form a plurality of projections on the first, tissue-facing side of the membrane, the plurality of projections defining the at least one channel.

16. The system of claim 14, wherein the membrane comprises a porous material.

17. The system of claim 14, wherein the plurality of matched deviations allow variation of the type of force applied to tissue on opposite sides of the membrane.

18. The system of claim 14, wherein the plurality of matched deviations deviate from a medial plane associated with the membrane.

19. The system of claim 14, wherein the plurality of non-planar, matched deviations on opposite sides of the membrane have substantially triangular faces.

20. The system of claim 14, wherein the plurality of non-planar, matched deviations on opposite sides of the membrane form a plurality of interconnected channels between the deviations.

21. A system for applying reduced pressure to a subcutaneous tissue site, the system comprising:
   a reduced-pressure source operable to supply reduced pressure;

a bioabsorbable membrane consisting essentially of one layer and having substantially no through openings and a substantially uniform membrane wall thickness and a first, tissue-facing surface, the membrane being shaped to form a plurality of protrusions on the tissue-facing surface, the plurality of protrusions at least partially defining at least one channel operable to transfer the reduced pressure along the tissue-facing surface;

a coating at least partially covering the membrane; and a delivery tube coupled to the membrane, the delivery tube operable to deliver the reduced pressure to the tissue-facing surface of the membrane.

22. The system of claim 21, wherein the membrane includes a second surface opposite the tissue-facing surface, and wherein each of the plurality of protrusions form a respective recess on the second surface.

23. The system of claim 21, wherein the membrane includes a groove on the tissue-facing surface of the membrane, wherein the groove is shaped to at least partially surround the delivery tube.

24. The system of claim 23, wherein the delivery tube is at least partially disposed in a groove associated with the membrane.

25. The system of claim 24, wherein the plurality of protrusions are a plurality of elongated protrusions.

26. The system of claim 25, wherein each of the plurality of elongated protrusions are substantially perpendicular to the groove, and wherein the plurality of elongated protrusions are substantially parallel to one another.

27. The system of claim 25, wherein at least a portion of the plurality of elongated protrusions have a first end and a second end, and wherein the first end is adjacent the groove, and wherein the second end is adjacent an edge of the membrane.

28. The system of claim 27, wherein the portion of the plurality of elongated protrusions radially extend from a portion of the groove.

29. The system of claim 25, wherein the at least one channel is a plurality of elongated channels, and wherein the plurality of elongated protrusions form the plurality of elongated channels, wherein each of the plurality of elongated channels have a channel first end and a channel second end, and wherein the channel first end is adjacent the groove, and wherein the channel second end is adjacent an edge of the membrane.

30. The system of claim 21, wherein the plurality of protrusions have substantially triangular faces.

31. The system of claim 21, wherein the at least one channel is a plurality of interconnected channels between the protrusions.

* * * * *